US00PP22602P2

(12) United States Plant Patent
Blom

(10) Patent No.: US PP22,602 P2
(45) Date of Patent: Mar. 20, 2012

(54) *ECHINACEA* PLANT NAMED 'MARMALADE'

(50) Latin Name: *Echinacea hybrida*
Varietal Denomination: Marmalade

(76) Inventor: Arie Blom, Oudewater (NL)

( * ) Notice: Subject to any disclaimer, the term of this patent is extended or adjusted under 35 U.S.C. 154(b) by 0 days.

(21) Appl. No.: 12/807,820

(22) Filed: Sep. 14, 2010

(51) Int. Cl.
*A01H 5/00* (2006.01)

(52) U.S. Cl. ..... Plt./428
(58) Field of Classification Search ..... Plt./428
See application file for complete search history.

*Primary Examiner* — Susan McCormick Ewoldt
(74) *Attorney, Agent, or Firm* — C. A. Whealy

(57) ABSTRACT

A new and distinct cultivar of *Echinacea* plant named 'Marmalade', characterized by its upright plant habit; moderately vigorous growth habit; freely basal branching habit; strong flowering stems; early and freely flowering habit; and large anemone-type inflorescences with orange-colored ray and disc florets.

3 Drawing Sheets

Botanical designation: *Echinacea hybrida.*
Cultivar denomination: 'MARMALADE'.

BACKGROUND OF THE INVENTION

The present invention relates to a new and distinct cultivar of *Echinacea* plant, botanically known as *Echinacea hybrida*, and hereinafter referred to by the name 'Marmalade'.

The new *Echinacea* plant is a product of a planned breeding program conducted by the Inventor in Vleuten and Zuidwolde, The Netherlands. The objective of the breeding program is to develop new freely branching and flowering *Echinacea* plants with attractive ray and disc floret coloration.

The new *Echinacea* plant originated from an open-pollination in July, 2006 in Vleuten, The Netherlands of a proprietary selection of *Echinacea hybrida* identified as code number Ec 555-016, not patented, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled environment in Zuidwolde, The Netherlands in July, 2008.

Asexual reproduction of the new *Echinacea* plant by micropropagation a controlled environment in Heerhugowaard, The Netherlands since July, 2008, has shown that the unique features of this new *Echinacea* plant are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Marmalade'. These characteristics in combination distinguish 'Marmalade' as a new and distinct cultivar of *Echinacea* plant:

1. Upright plant habit.
2. Moderately vigorous growth habit.
3. Freely basal branching habit.

4. Strong flowering stems.
5. Early and freely flowering habit.
6. Large anemone-type inflorescences with orange-colored ray and disc florets.

Plants of the new *Echinacea* can be compared to plants of the female parent selection. Plants of the new *Echinacea* differ from plants of the female parent selection in the following characteristics:

1. Plants of the new *Echinacea* are more freely branching than plants of the female parent selection.
2. Plants of the new *Echinacea* flower earlier than plants of the female parent selection.
3. Plants of the new *Echinacea* have larger inflorescences than plants of the female parent selection.

Plants of the new *Echinacea* can be compared to plants of *Echinacea hybrida* 'Razzmatazz', disclosed in U.S. Plant Pat. No. 13,894. In side-by-side comparisons, plants of the new *Echinacea* differed from plants of 'Razzmatazz' in the following characteristics:

1. Plants of the new *Echinacea* were more freely branching than plants of 'Razzmatazz'.
2. Plants of the new *Echinacea* flowered earlier than plants of 'Razzmatazz'.
3. Plants of the new *Echinacea* and 'Razzmatazz' differed in floret coloration as plants of 'Razzmatazz' had dark pink-colored ray florets and red purple-colored disc florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Marmalade' grown in a container.

The photograph on the second sheet is a close-up view of a typical inflorescence of 'Marmalade'.

The photograph on the third sheet is a close-up view of the upper surface of a typical leaf of 'Marmalade'.

DETAILED BOTANICAL DESCRIPTION

The aforementioned photographs and following observations and measurements describe plants grown during the summer in an outdoor nursery in Zuidwolde, The Netherlands and under conditions and practices which approximate those generally used in commercial *Echinacea* production. During the production of the plants, day temperatures ranged from 15° C. to 32° C. and night temperatures ranged from 8° C. to 18° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Marmalade'.

Parentage:

*Female parent.*—Proprietary selection of *Echinacea hybrida* identified as code number Ec 555-016, not patented.

*Male parent.*—Unknown selection of *Echinacea hybrida*, not patented.

Propagation:

*Type.*—By micropropagation.

*Time to initiate roots, summer.*—About one week at 25° C.

*Time to produce a rooted young plant, summer.*—About five weeks at 21° C.

*Root description.*—Fine, fibrous; pale cream in color.

*Rooting habit.*—Freely branching; moderately dense.

Plant description:

*Plant form/growth habit.*—Herbaceous perennial; upright and columnar plant habit, broad inverted triangle; freely basal branching habit; moderately vigorous growth habit.

*Plant height.*—About 53.6 cm.

*Plant diameter or spread.*—About 56.5 cm.

*Basal branches.*—Length: About 50.8 cm. Diameter: About 5 mm. Internode length: About 5.6 cm. Aspect: About 45° from vertical. Strength: Strong. Texture: Sparsely pubescent, strigose; rough. Color: Close to 144C.

Foliage description:

*Arrangement.*—Alternate, simple.

*Length.*—About 10.3 cm.

*Width.*—About 8.8 cm.

*Shape.*—Narrowly ovate to lanceolate.

*Apex.*—Narrowly acute.

*Base.*—Long attenuate to narrowly cuneate.

*Margin.*—Entire.

*Texture, upper and lower surfaces.*—Sparsely pubescent, strigose; rough.

*Venation pattern.*—Pinnate.

*Color.*—Developing leaves, upper surface: Close to 137B. Developing leaves, lower surface: Close to 137C. Fully expanded leaves, upper surface: Close to 147A; venation, close to 144A. Fully expanded leaves, lower surface: Close to N137B; venation, close to 144B.

*Petioles.*—Length: About 2.7 cm. Diameter: About 3.5 mm. Texture, upper and lower surfaces: Smooth, glabrous. Color, upper surface: Close to 144B to 144C. Color, lower surface: Close to 144C.

Inflorescence description:

*Appearance.*—Rotate anemone-type inflorescence form with ray and disc florets arranged acropetally on a capitulum; inflorescences positioned upright above the foliar plane on strong peduncles.

*Quantity of inflorescences per plant.*—About twelve.

*Fragrance.*—Moderate; sweetly acidic, pleasant.

*Time to flower.*—Plants flower continuously from early July to late September in The Netherlands.

*Inflorescence longevity.*—Inflorescences maintain good substance for about three weeks on the plant; inflorescences not persistent.

*Inflorescence bud.*—Height: About 1.7 cm. Diameter: About 2.2 cm. Shape: Flattened globular. Color: Close to 146C to 146D.

*Inflorescence size.*—Diameter: About 6.4 cm. Depth (height): About 5.6 cm. Disc diameter: About 6.4 cm. Receptacle height: About 8 mm. Receptacle diameter: About 8 mm. Receptacle color: Close to 157D.

*Ray florets.*—Length: About 5.1 cm. Width: About 9 mm. Shape: Narrowly oblanceolate. Apex: Praemorse. Base: Cuneate. Margin: Entire. Texture, upper and lower surfaces: Smooth, glabrous; longitudinally ridged. Number of ray florets per inflorescence: About twelve arranged in a single whorl. Aspect: Drooping, about 60° from horizontal. Color: When opening, upper surface: Close to N25A to N25B. When opening, lower surface: Close to 34C to 34D; towards the apex and base, tinged with close to 150D. Fully opened, upper surface: Close to 26A; with development, color becoming closer to 162A. Fully opened, lower surface: Close to 144B to 144C with mid-section strongly tinged with close to 34D; with development, color becoming closer to 144D with mid-section strongly tinged with close to 162A.

*Disc florets.*—Length: About 2.5 cm. Diameter: About 6 mm. Shape: Tubular, enlarged; apices praemorse. Number of disc florets per inflorescence: About 200. Texture, upper and lower surfaces: Smooth, glabrous. Color: Immature, inner surface: Close to N25A; towards the base, close to 53A. Immature, outer surface: Close to 151D; towards the apex, tinged with close to 34B. Mature, inner surface: Close to 162A. Mature, outer surface: Close to 144D; mid-section strongly tinged with close to 162A.

*Receptacle spines.*—Quantity: One per disc floret. Shape: Acicular. Apex: Acute. Base: Attenuate. Texture: Smooth, glabrous. Color: Apex: Close to 46A. Mid-section: Close to 143B. Base: Close to 145D.

*Involucral bracts.*—Quantity per inflorescence: About 36 in about two whorls. Length: About 8 mm. Width: About 5 mm. Shape: Ovate. Apex: Acute. Base: Cuneate. Margin: Entire. Texture, upper surface: Smooth, glabrous. Texture, lower surface: Sparsely pubescent along the margins. Color, upper and lower surfaces: Close to 137B.

*Peduncles.*—Length, terminal peduncle: About 9.4 cm. Diameter: About 4 mm. Strength: Strong. Aspect: Upright to about 30° from vertical. Texture: Sparsely pubescent, strigose. Color: Close to 144C.

*Reproductive organs.*—Androecium (present on ray and disc florets): Quantity per floret: About four. Filament length: About 3 mm. Filament color: Close to N155B to N155C. Anther shape: Oblong, short. Anther length: About 1 mm. Anther color: Close to N199B. Pollen amount: Scarce. Pollen color: Greyed yellow. Gynoecium (present only on disc florets): Quantity per floret: One. Pistil length: About 5 mm. Stigma shape: Decurrent. Stigma color: Close to 144A to 144B. Style length: About 4 mm. Style color: Close to 144A to 144B. Ovary color: Close to 157A to 157B. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind and have been observed to tolerate high temperatures of about 35° C. and hardy to USDA Hardiness Zone 4.

It is claimed:

1. A new and distinct *Echinacea* plant named 'Marmalade' as illustrated and described.

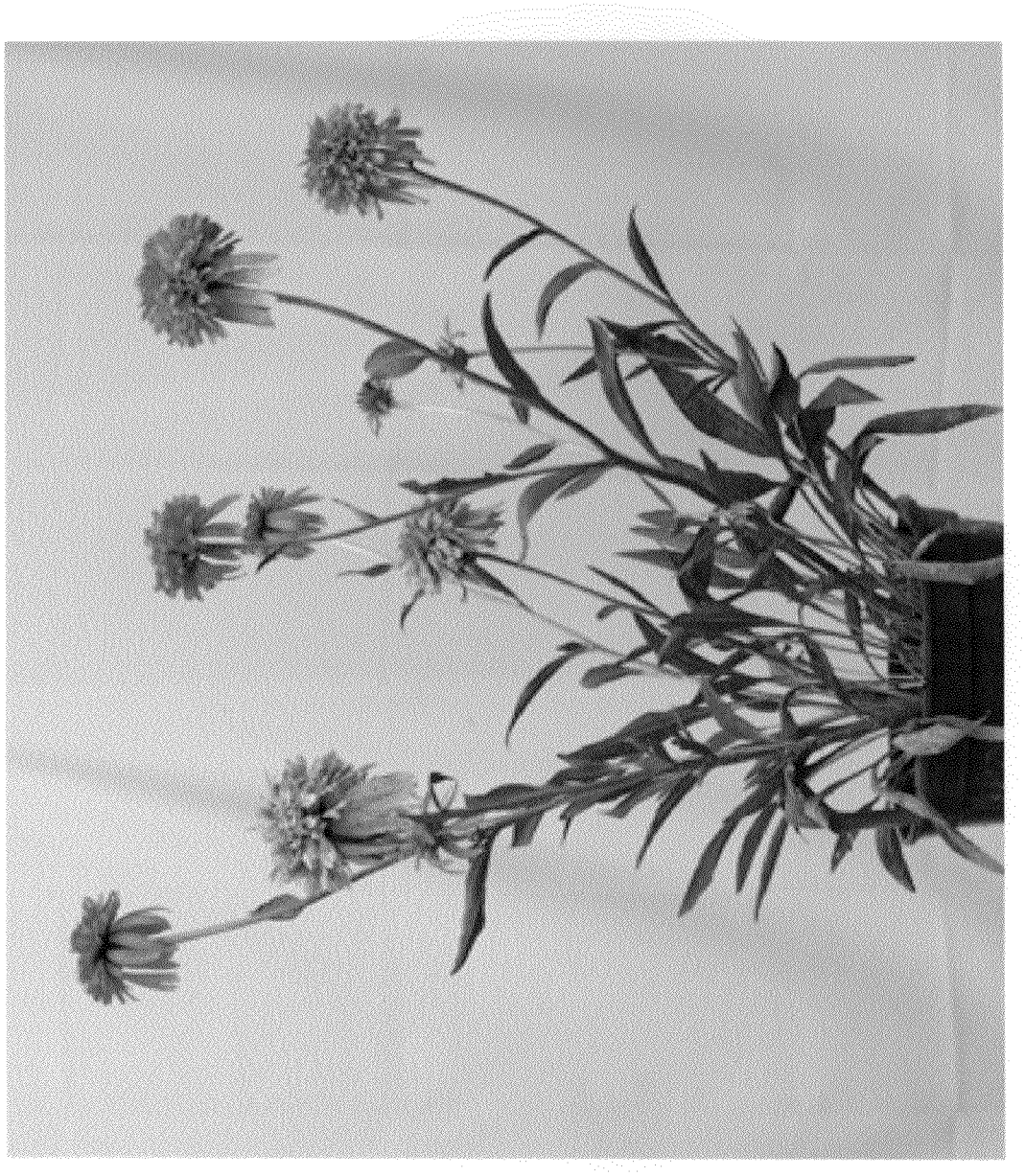

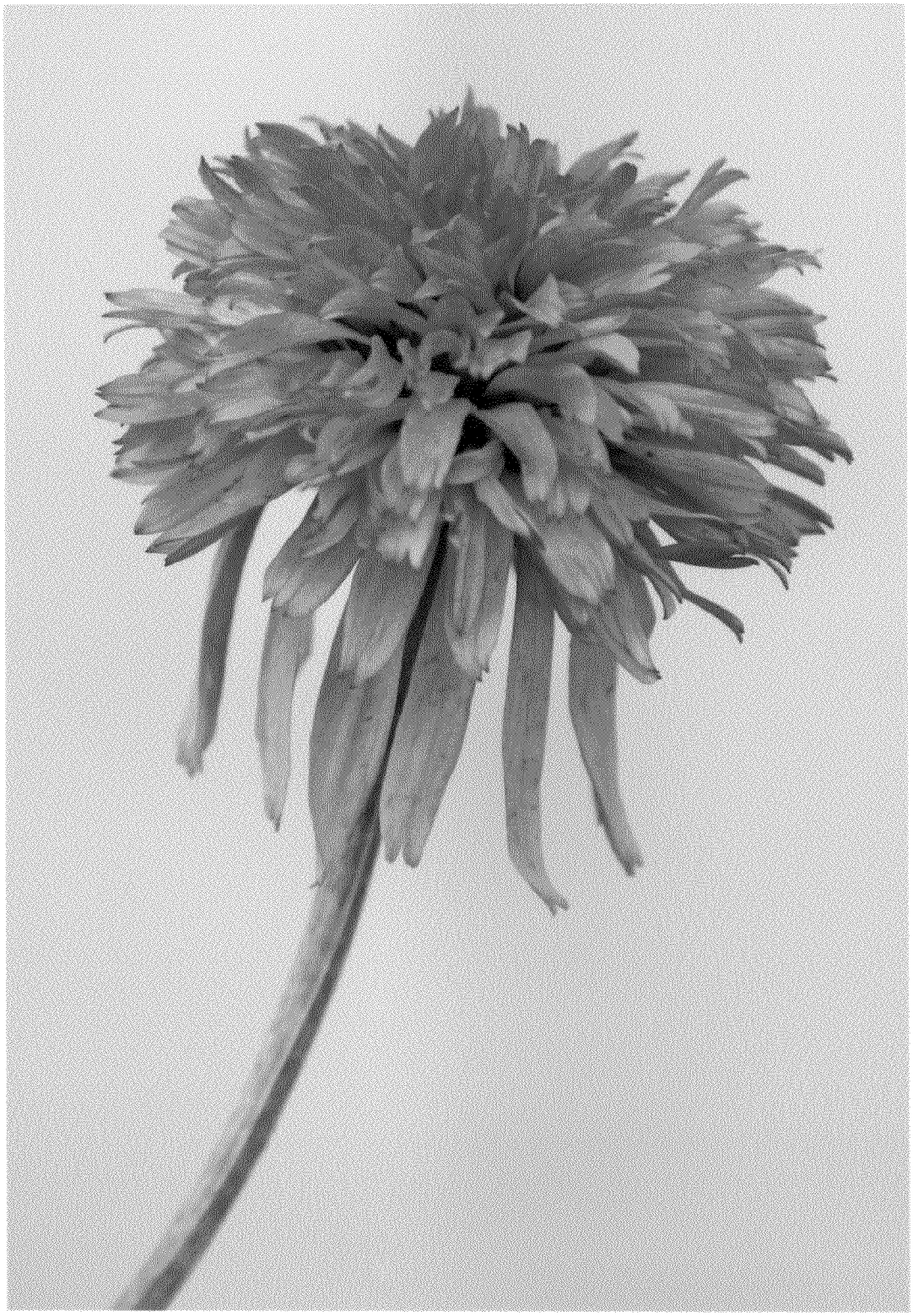

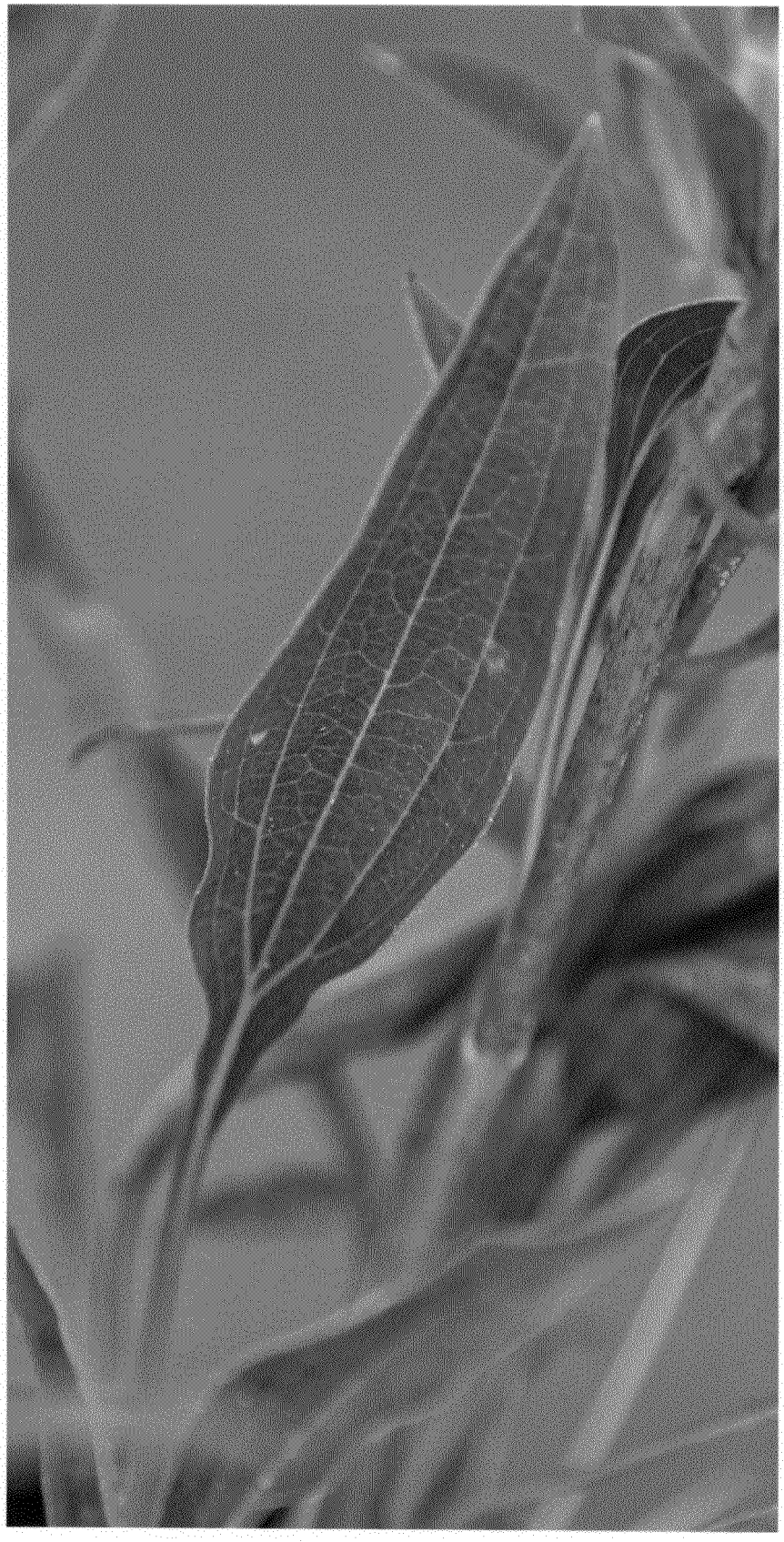

* * * * *